United States Patent [19]

Fujino et al.

[11] 3,976,513
[45] Aug. 24, 1976

[54] METHOD FOR JUDGING THE FITNESS OF A STEEL COMPOSITION TO A CASTING PRACTICE

[75] Inventors: Nobukatsu Fujino, Kobe; Kazuo Yamanaka, Toyonaka; Takeo Harada, Nishinomiya, all of Japan

[73] Assignee: Sumitomo Metal Industries, Ltd., Japan

[22] Filed: Feb. 21, 1975

[21] Appl. No.: 551,650

[30] Foreign Application Priority Data
Feb. 21, 1974  Japan.............................. 49-21170
Feb. 21, 1974  Japan.............................. 49-21169

[52] U.S. Cl.................................. 148/2; 29/527.7; 148/12 R; 164/4
[51] Int. Cl.²...................... B22D 25/06; C21D 7/14
[58] Field of Search.......................... 148/2, 3, 12 R; 29/527.7; 164/4

[56] References Cited
UNITED STATES PATENTS

| | | | |
|---|---|---|---|
| 3,127,642 | 4/1964 | Zaeytydt................................ | 164/4 |
| 3,367,189 | 2/1968 | Curry, Jr................................ | 164/4 |
| 3,478,808 | 11/1969 | Adams.................................... | 164/4 |
| 3,523,833 | 8/1970 | Kroneis et al........................... | 148/2 |
| 3,779,646 | 12/1973 | Hancart et al........................... | 164/4 |

Primary Examiner—W. Stallard
Attorney, Agent, or Firm—Watson, Cole, Grindle & Watson

[57] ABSTRACT

Herein disclosed is a method and an apparatus for judging the fitness of a steel composition for a particular casting practice in order to prevent excessive segregation of manganese and phosphorous in the course of the casting. We have discovered that the simultaneous segregation of manganese and phosphorous tends to cause the formation of bainite and/or martensite in steel plate product during the cooling of the steel plate after rolling. When the manganese and phosphorous concentrations satisfy the following requirement (1):

$$Mn\ (\%) \times P\ (\%) < 0.60/f \ldots \qquad (1)$$

wherein $f$ denotes the segregation factor of the particular casting practice, regarding the product of Mn (%) and P (%), the formation of bainite and/or martensite is prevented. Accordingly, it is possible to predict the fitness of the molten steel to the particular casting practice.

1 Claim, 3 Drawing Figures

METHOD FOR JUDGING THE FITNESS OF A STEEL COMPOSITION TO A CASTING PRACTICE

This invention relates to a method for judging whether of not, the chemical composition of a molten steel is suitable for a particular casting practice in order to ensure the manufacture of steel plate products having metallurgically uniform structures.

A steel plate product sometimes includes a metallurgically nonuniform portion which consists of bainite and/or martensite and, therefore, has an abnormally higher hardness and a poorer toughness than the remaining portion which is formed of ferrite and/or pearlite. Particularly, in the steel plate products manufactured by the continuous casting method, such a metallurgically heterogeneous structure is often encountered forming a thin layer of about 50μ width at the mid position in the direction of thickness.

This metallurgically nonuniform portion in a steel plate product results mainly from segregation. "Segregation" is the nonuniform concentration of alloying constituents and impurities which arises during the solidification of steel. Since the axial portion of an ingot or a slab solidifies much later than the outer parts, it generally contains a higher proportion of alloying constituents and impurities of lower freezing points than the rest of the ingot or slab. Such segregation, of course, results in nonuniformities in the composition in the final steel product. When segregation develops to a large extent, however, not only nonuniformity in concentration, but also in metallurgical structure is often caused even though the as-rolled steel plate is cooled at a very low cooling rate. This is experienced in the cases where the as-rolled steel plate is allowed to cool spontaneously or is air cooled so that the middle portion of the plate cools at a rate of less than 6°C/sec. Needless to say, the formation of this heterogeneous structure is deleterious to the mechanical properties of the steel plate product and sometimes results in the failure thereof.

An object of this invention is to provide a method for judging the fitness of a steel composition to a particular casting practice in order to suppress the segregation in the steel to an extent that the abovementioned heterogeneous structure is not formed in the final steel product.

Other objects and features of this invention will be apparent from the following description taken in connection with the accompanying drawing wherein.

Figure 1:
FIG. 1 is a block diagram of the apparatus according to this invention.

This invention is directed to the control of steel casting in steel plate manufacture. As described, steel plate products sometimes include metallurgically nonuniform portions which deleteriously affect the mechanical properties and, thus, sometimes resulting in the failure of the products. Generally, bainite and/or martensite appears when the steel is quenched from the austenitic temperature range. However, the segregated composition sometimes is transformed into bainite and/or martensite even when the steel plate is cooled slowly such as when it is allowed to cool spontaneously or to be air cooled. In such spontaneous cooling, the middle or segregated position is supposed to cool at a rate of less than 6°C/sec in the case of plates of 15mm thickness.

Such a nonuniform structure of steel plate has been often encountered in the manufacture of steel plate having a thickness of at least 15mm and a basic composition of carbon 0.10 ~ 0.40 weight %, silicon 0.10 ~ 0.50 weight %, manganese 0.05 ~ 3.0 weight %, the balance being iron, and optionally containing strengthening elements such as Cr, Ni, Cu, Mo, Ti, V and Nb. Therefore, this invention is directed to an improvement of the casting in the manufacture of the steel plate above-mentioned.

After considerable research, we have discovered that the heterogeneous structure of bainite and/or martensite appears only when the manganese and phosphorous segregate simultaneously to a certain extent. Alloying elements and impurities other than manganese and phosphorous, such as silicon and sulfur, also segregate during the solidification of steel; however, these segregations do not have as much influence on the above-mentioned formation of bainite and/or martensite. We also have found that if the product of concentrations, in percent of manganese and phosphorous at the segregated composition is larger than 0.60, the segregated portion is transformed into bainite and/or martensite even when the steel is cooled at a rate of less than 6°C/sec from the austenitic temperature range. Thus, it becomes possible to prevent the formation of bainite and/or martensite by adjusting the degree of segregation of manganese and phosphorous. It becomes also possible to predict whether or not a molten steel of a particular chemical composition will cause segregation in a particular casting practice to such an extent that the heterogeneous metallurgical structure is formed in the later cooling step. If a molten steel is judged as one developing segregation in the selected casting practice to the extent of causing the formation of the heterogeneous structure subsequent cooling step, the casting of said molten steel should not be conducted, or another casting practice should be employed in place of the previously selected casting practice.

As is well-known, the concentration at the segregated position has the following relationship to the average concentration;

$C_s = f_c C_a$ $f_C$ : segregation ratio
$C_S$ : concentration at the segregated composition and
$C_A$ : average concentration over the total steel.

The segregation ratio depends upon the condition under which the steel solidifies. Accordingly, the above-mentioned requirement that the heterogeneous structure is not formed is expressed as follows:

$$Mn (\%) \times P (\%) > 0.60/f \ldots \quad (1)$$

$$f = fM \cdot fP \ldots \quad (2)$$

Mn (%): average concentration of manganese in the molten steel to be cast
P (%): average concentration of phosphorous in the molten steel to be cast
$f$: segregation factor regarding the product of Mn (%) and P (%)
$fM$: manganese segregation ratio
$fP$: phosphorous segregation ratio The average concentrations, P (%) and Mn (%), of a molten steel can be readily and rapidly determined by well-known methods such as emission spectroanalysis fluorescent X-ray analysis.

As mentioned above, the segregation factor $f$ depends upon the solidification conditions and is expressed as follows:

$$f = \frac{\text{Product of the concentrations of Mn(\%) and P(\%) at the segregated position}}{\text{Product of the average concentrations of Mn(\%) and P(\%)}}$$

Thus, the factor $f$ of any casting practice can be obtained from the chemical analysis of the molten steel and the segregated position of a solidified ingot or slab. The factor $f$ must be calculated before conducting the method of this invention.

From the results of EPMA (electron probe microanalyzer measurements) measurement on ingots and slabs obtained from various casting practices, the segregation factor $f$ is obtained as illustrated in Table I.

Table I

| Casting practice | Segregation factor $\zeta$ |
| --- | --- |
| Continuous casting of 150~300mm thick slab | 15 ~ 23 |
| Casting by 10~35t mold | 12 ~ 20 |
| Casting by 3~10t mold | 6 ~ 12 |

As a factor which contributes to the formation of heterogeneous structure (bainite and/or martensite), manganese concentration should be replaced a manganese equivalent (Mn equiv.) theoretically. Manganese equivalent (Mn equiv.) is expressed as follows:

$$\text{Mn equiv.} = (\text{Mn} + 0.39\text{C} + 0.10\text{Si} - 0.04\text{S} + 1.33\text{P} + 0.13\text{Cr} + 0.08\text{Ni} + 0.07\text{Cu} + 0.23\text{Mo} + 0.05\text{Nb})$$

as such, requirement (1) should be rewritten to the following (1)'

$$\text{Mn equiv.} \times \text{P (\%)} < 0.60/f \ldots \qquad (1)'$$

However, since the contribution of the other elements is very small and is practically negligible, we employ the product of Mn and P concentrations in lieu of Mn equiv. × P for conducting this invention.

In the steel making process now conducted on a mass-scale in Japan, phosphorous removal is effected by convertor or open-hearth furnace to the degree of 0.03 to 0.06%. Therefore, in adjusting the steel composition to satisfy the requirement (1), it is necessary to decrease the manganese content preferentially. Manganese is a strengthening element, and as such, a decrease in manganese content results in a decrease in the tensile strength of the resulting steel plate. For compensating such a decrease in tensile strength, at least one strengthening element such as Cr, Ni, Cu, Mo, Ti, V and Nb may be added to the molten steel. This addition should be effected in such amounts that the value of the following formula (3) below is equal to the required tensile strength of the final steel plate product.

$$\text{T.S (kg/mm}^2\text{)} = 61.0 \times (C \times 1/5\text{Mn} + 1/7\text{Si} + \tfrac{2}{3}\text{P} + 1/7\text{Cu} + 1/20\text{Ni} + 1/9\text{Cr} + \tfrac{1}{2}\text{V} + \tfrac{1}{2}\text{Mo} + \tfrac{3}{4}\text{Nb}) \times 24.3 \ldots \qquad (3)$$

Now referring to FIG. 1, an apparatus according to this invention is explained in detail. The illustrated apparatus is designed so as to determine whether or not the chemical composition of a molten steel is fit for a particular casting practice. That is, whether or not segregation in the steel in the course of said particular casting practice would cause the formation of bainite and/or martensite in the subsequent cooling step of the as-rolled steel plate. The apparatus includes a chemical analyzer 11 which can rapidly analyze the chemical composition of molten steel such as an emission spectroanalyzer or a fluorescent X-ray analyzer. To the output of the analyzer 11, a multiplier 12 is connected. Multiplier 12 is designed to read the values of the manganese and phosphorous concentrations, Mn (%) and P (%), and to calculate the product of Mn (%) and P (%). To the output of the multiplier 12, a comparator 13 is connected wherein the value of the product of Mn (%) and P (%) is compared to the value of $0.60/f$. The Segregation factor $f$ is determined earlier for the employed casting practice in the manner mentioned above and is preset in comparator 13. If the value of the product of Mn (%) and P (%) of the particular lot of molten steel is larger than $0.60/f$, the comparator 13 operates a warning means 14 so that an operator can stop the casting of the particular lot. Thus, excessive segregation of manganese and phosphorous which causes the formation of heterogeneous metallurgical structure in the steel plate product is suppressed.

Examples will be described now in order to show the effects of this invention;

EXAMPLE I

Samples of molten steel having the partial chemical compositions as shown in Table II were cast by a continuous casting machine.

Table II

| Sample No. | Chemical composition | | | | | Sol.Al | Mn × P |
| --- | --- | --- | --- | --- | --- | --- | --- |
|  | C | Si | Mn | P | S | | |
| A-1 | 0.14 | 0.36 | 1.48 | 0.030 | 0.007 | 0.022 | 0.044 |
| A-2 | 0.20 | 0.01 | 1.50 | 0.025 | 0.005 | 0.012 | 0.037 |
| A-3 | 0.15 | 0.01 | 1.36 | 0.031 | 0.005 | 0.009 | 0.042 |
| A-4 | 0.18 | 0.39 | 1.43 | 0.030 | 0.009 | 0.020 | 0.042 |
| A-5 | 0.09 | 0.10 | 1.21 | 0.029 | 0.019 | 0.018 | 0.035 |
| A-6 | 0.07 | 0.24 | 1.40 | 0.025 | 0.018 | 0.020 | 0.035 |
| A-7 | 0.13 | 0.29 | 1.41 | 0.028 | 0.009 | 0.031 | 0.039 |
| A-8 | 0.15 | 0.37 | 1.45 | 0.007 | 0.008 | 0.036 | 0.010 |
| A-9 | 0.14 | 0.43 | 0.45 | 0.017 | 0.016 | 0.045 | 0.007 |
| A-10 | 0.12 | 0.36 | 1.26 | 0.010 | 0.008 | 0.015 | 0.013 |
| A-11 | 0.18 | 0.40 | 1.30 | 0.010 | 0.010 | 0.040 | 0.013 |
| A-12 | 0.12 | 0.30 | 0.44 | 0.025 | 0.009 | 0.024 | 0.011 |
| A-13 | 0.20 | 0.25 | 0.37 | 0.028 | 0.008 | 0.045 | 0.010 |

During the solidification of steel by this continuous casting machine, the maximum segregation ratio of manganese was 2.0 and that of phosphorous was 11.5.

Thus, the maximum segregation factor $f$ is 23 and the requirement (1) described hereinbefore becomes as follows;

$$\text{Mn } (\%) \times \text{P } (\%) < 0.60/23 = 0.026 \ldots \quad (4)$$

Figure 2:
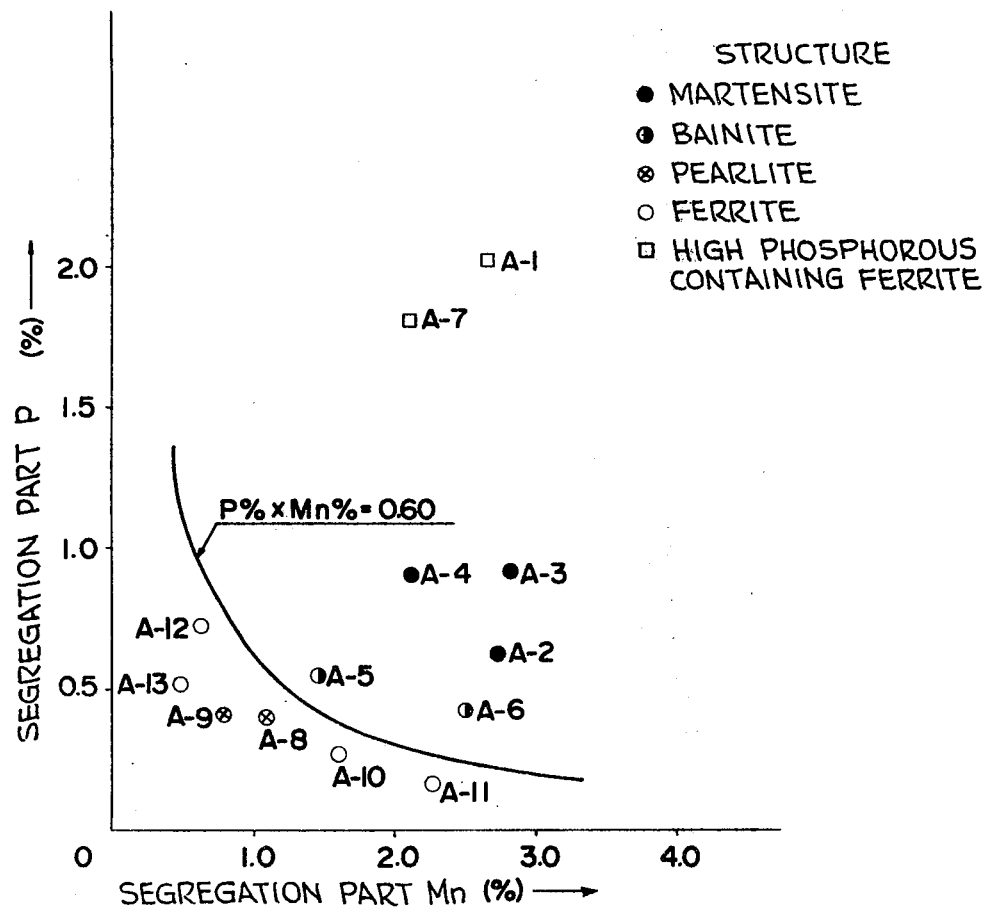
FIGS. 2 and 3 illustrate the relationship among the concentrations of manganese and phosphorous at the segregated composition, and the metallurgical structure at that composition.

The cast steel slabs were rolled into plates and then cooled at a cooling rate such that the center of the plate was cooled at a rate lower than 6°C/sec. EPMA measurement was conducted on manganese and phosphorous concentrations at segregated position of each resulting steel plate, and microscopic observation was conducted to determine the metallurgical structure of each segregated position. The results are shown in Table III and FIG. 2.

Table III

| Sample No. | Concentration (%) at segregation position Mn | P | Metallurgical structure |
|---|---|---|---|
| A - 1 | 2.63 ~ 2.88 | 1.95 ~ 3.05 | Nonuniform structure |
| A - 2 | 2.75 ~ 2.85 | 0.53 ~ 0.70 | Nonuniform structure |
| A - 3 | 2.75 ~ 2.90 | 0.89 ~ 0.94 | Nonuniform structure |
| A - 4 | 2.08 ~ 2.19 | 0.75 ~ 0.81 | Nonuniform structure |
| A - 5 | 1.41 ~ 1.55 | 0.50 ~ 0.57 | Nonuniform structure |
| A - 6 | 2.48 ~ 2.60 | 0.40 | Nonuniform structure |
| A - 7 | 2.15 ~ 2.20 | 1.80 | Nonuniform structure |
| A - 8 | 1.05 ~ 1.15 | 0.37 ~ 0.40 | Uniform structure |
| A - 9 | 0.78 ~ 0.88 | 0.33 ~ 0.43 | Uniform structure |
| A - 10 | 1.60 ~ 1.66 | 0.25 ~ 0.30 | Uniform structure |
| A - 11 | 2.25 ~ 2.35 | 0.17 ~ 0.22 | Uniform structure |
| A - 12 | 0.58 ~ 0.68 | 0.70 ~ 0.75 | Uniform structure |
| A - 13 | 0.45 ~ 0.55 | 0.50 | Uniform structure |

The above results show that the steel samples Nos. A-1 ~ A-7 did noft satisfy requirement (4) and caused the formation of a heterogeneous metallurgical structure of abnormally high hardness and poor toughness at the segregated position of the steel plate product, while the steel samples Nos. A-8 ~ A-13 satisfied requirement (4) and did not cause the formation of such heterogeneous structure. The segregated portions of samples Nos. A-1 ~ A-7 included martensite of a hardness of $H_v450$ ~ 600, while the segregated portions of samples Nos. A-8 ~ A-13 consisted of the same structure as the remaining portions, i.e., ferrite and/or pearlite, of a hardness in the order of $H_v200$.

Accordingly, the validity of requirements (1) and (4) was empirically ascertained.

EXAMPLE 2

Samples of molten steel having the partial chemical compositions as shown in Table IV were cast by continuous casting machines, 10 ~ 30$t$ molds and 3 ~ 10$t$ molds into ingots or slabs.

Table IV

| Sample No. | Chemical composition (%) | | | | | | | | | | |
|---|---|---|---|---|---|---|---|---|---|---|---|
| | C | Si | Mn | P | Cr | Ni | Cu | Nb | V | S | SolAl |
| B-1 | 0.20 | 0.25 | 0.50 | 0.006 | 0.03 | — | — | — | — | 0.03 | 0.04 |
| B-2 | " | " | " | " | " | 4.0 | 0.10 | — | — | " | " |
| B-3 | 0.20 | 0.25 | 0.50 | 0.01 | 0.50 | 4.0 | 0.10 | — | 0.3 | 0.03 | 0.04 |
| B-4 | " | 0.45 | " | " | 0.03 | 9.8 | " | 0.10 | " | " | " |
| B-5 | 0.40 | " | " | " | 0.97 | " | 0.40 | — | — | " | " |
| B-6 | 0.20 | 0.25 | " | 0.05 | 0.03 | 0.40 | 0.10 | — | — | " | " |
| B-7 | " | " | " | 0.07 | " | " | " | — | — | " | " |
| B-8 | " | " | " | 0.10 | " | " | " | — | — | " | " |
| B-9 | " | " | 1.50 | 0.006 | 0.03 | — | — | — | — | " | " |
| B-10 | " | " | " | " | " | 4.0 | 0.10 | — | — | " | " |
| B-11 | " | " | " | 0.01 | 0.50 | " | " | — | 0.3 | " | " |
| B-12 | " | 0.45 | " | " | 0.03 | 9.8 | " | 0.10 | " | " | " |
| B-13 | 0.40 | " | " | " | 0.97 | " | 0.40 | — | — | " | " |
| B-14 | 0.20 | 0.25 | " | 0.05 | 0.03 | 0.40 | 0.10 | — | — | " | " |
| B-15 | " | " | " | 0.06 | " | " | " | — | — | " | " |
| B-16 | " | " | " | 0.10 | " | " | " | — | — | " | " |
| B-17 | 0.20 | 0.25 | 3.00 | 0.006 | 0.03 | — | — | — | — | 0.03 | 0.04 |
| B-18 | " | " | " | " | " | 4.0 | 0.10 | — | — | " | " |
| B-19 | " | " | " | 0.01 | 0.50 | " | " | — | 0.3 | " | " |
| B-20 | " | 0.45 | " | " | 0.03 | 9.8 | " | 0.10 | " | " | " |
| B-21 | 0.40 | " | " | " | 0.97 | " | 0.40 | — | — | " | " |
| B-22 | 0.20 | 0.25 | " | 0.03 | 0.03 | 0.40 | 0.10 | — | — | " | " |
| B-23 | " | " | " | 0.07 | " | " | " | — | — | " | " |
| B-24 | " | " | " | 0.10 | " | " | " | — | — | " | " |
| B-25 | " | " | 3.20 | 0.006 | " | — | — | — | — | " | " |
| B-26 | " | " | " | " | " | 4.0 | 0.10 | — | — | " | " |
| B-27 | 0.20 | 0.25 | 3.20 | 0.01 | 0.03 | — | — | — | — | 0.03 | 0.04 |
| B-28 | " | " | 0.80 | 0.05 | " | — | — | — | — | " | " |
| B-29 | " | " | " | " | 0.50 | 4.0 | 0.10 | — | — | " | " |

The manganese and phosphorous concentrations at segregated positions of the cast steel ingots or slabs were determined by EPMA measurements. The maximum segregation factor $f$ for each casting and the metallurgical structure of each segregated position were also determined. These results are shown in Table V.

Figure 3:
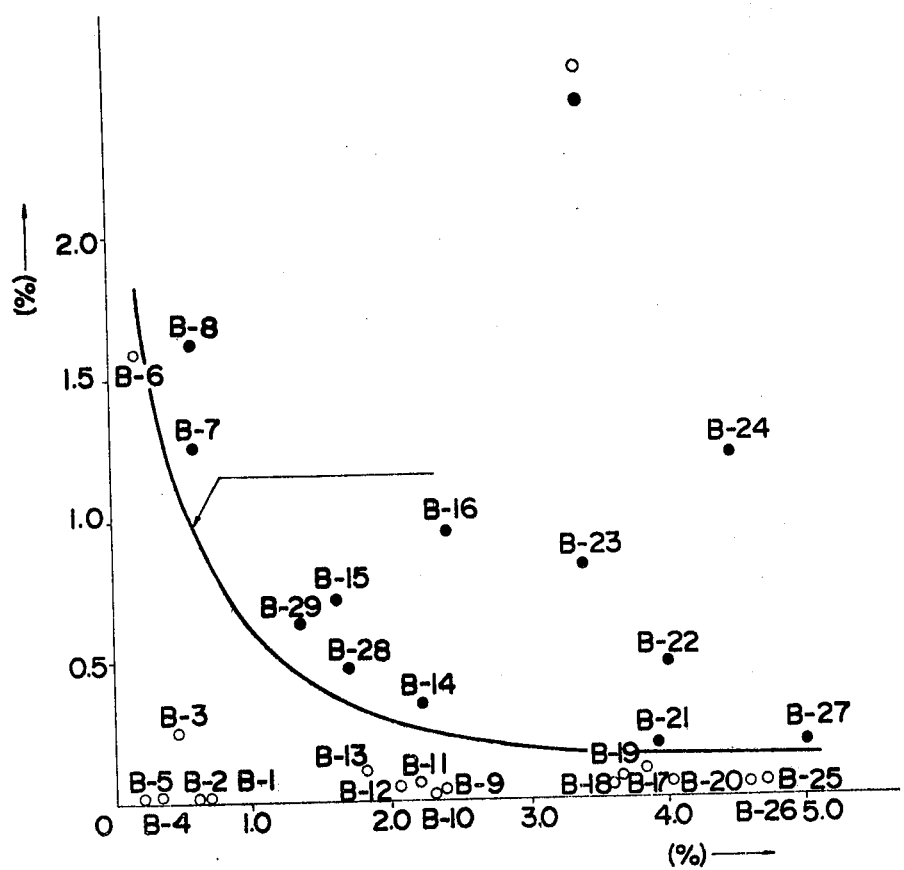

From the above results, it is readily understandable that when requirement (1) is satisfied, a metallurgically uniform structure is obtained even though segregations of manganese and phosphorous occur. The results of microscopic observations on the segregated positions of slabs manufactured by the continuous casting machine are illustrated in FIG. 3.

Table V

| | Continuous casting | | | | Large mold steel ingot | | | | Small mold steel ingot | | | |
|---|---|---|---|---|---|---|---|---|---|---|---|---|
| | Base | Segregation part | | | Base | Segregation part | | | Base | Segregation part | | |
| Sample No. | metal Mn×P | Mn×P | Max. segregation factor | Metallurgical structure | metal Mn×P | Mn×P | Max. segregation factor | Metallurgical structure | metal Mn×P | Mn×P | Max. segregation factor | Metallurgical structure |
| B-1 | 0.003 | 0.066 | 22 | Uniform structure | 0.003 | 0.060 | 20 | Uniform structure | 0.003 | 0.0036 | 12 | Uniform structure |
| B-2 | 0.003 | 0.057 | 19 | " | 0.003 | 0.054 | 18 | " | 0.003 | 0.0036 | 12 | " |
| B-3 | 0.005 | 0.095 | 19 | " | 0.005 | 0.090 | 18 | " | 0.005 | 0.055 | 11 | " |
| B-4 | 0.005 | 0.010 | 20 | " | 0.005 | 0.085 | 17 | " | 0.005 | 0.055 | 11 | " |
| B-5 | 0.005 | 0.010 | 20 | " | 0.005 | 0.085 | 17 | " | 0.005 | 0.055 | 11 | " |
| B-6 | 0.025 | 0.550 | 22 | " | 0.025 | 0.400 | 16 | " | 0.025 | 0.300 | 12 | " |
| B-7 | 0.035 | 0.770 | 22 | Nonuniform structure | 0.035 | 0.595 | 17 | " | 0.035 | 0.280 | 8 | " |
| B-8 | 0.050 | 1.100 | 22 | " | 0.050 | 0.850 | 17 | Nonuniform structure | 0.050 | 0.400 | 8 | " |
| B-9 | 0.009 | 0.189 | 21 | Uniform structure | 0.009 | 0.171 | 19 | Uniform structure | 0.009 | 0.099 | 11 | " |
| B-10 | 0.009 | 0.162 | 18 | " | 0.009 | 0.171 | 19 | " | 0.009 | 0.099 | 11 | " |
| B-11 | 0.015 | 0.270 | 18 | " | 0.015 | 0.300 | 20 | " | 0.015 | 0.180 | 12 | " |
| B-12 | 0.015 | 0.315 | 21 | " | 0.015 | 0.240 | 16 | " | 0.015 | 0.180 | 12 | " |
| B-13 | 0.015 | 0.315 | 21 | " | 0.015 | 0.240 | 16 | " | 0.015 | 0.180 | 12 | " |
| B-14 | 0.075 | 1.125 | 15 | Nonuniform structure | 0.075 | 0.900 | 12 | Nonuniform structure | 0.075 | 0.525 | 7 | " |
| B-15 | 0.090 | 1.350 | 15 | " | 0.090 | 1.080 | 12 | " | 0.090 | 0.540 | 6 | " |
| B-16 | 0.150 | 2.250 | 15 | " | 0.150 | 1.950 | 13 | " | 0.150 | 0.900 | 6 | Nonuniform structure |
| B-17 | 0.018 | 0.414 | 23 | Uniform structure | 0.018 | 0.360 | 20 | Uniform structure | 0.018 | 0.198 | 11 | Uniform structure |
| B-18 | 0.018 | 0.360 | 20 | " | 0.018 | 0.342 | 19 | " | 0.018 | 0.216 | 12 | " |
| B-19 | 0.030 | 0.630 | 21 | Nonuniform structure | 0.030 | 0.480 | 16 | " | 0.030 | 0.240 | 8 | " |
| B-20 | 0.030 | 0.630 | 21 | " | 0.030 | 0.510 | 17 | " | 0.030 | 0.210 | 7 | " |
| B-21 | 0.030 | 0.630 | 21 | " | 0.030 | 0.540 | 18 | " | 0.030 | 0.210 | 7 | " |
| B-22 | 0.090 | 1.440 | 16 | " | 0.090 | 1.080 | 12 | Nonuniform structure | 0.090 | 0.540 | 6 | " |
| B-23 | 0.210 | 3.360 | 16 | " | 0.210 | 2.520 | 12 | " | 0.210 | 1.260 | 6 | Nonuniform structure |
| B-24 | 0.300 | 4.800 | 16 | " | 0.300 | 3.600 | 12 | " | 0.300 | 2.100 | 7 | " |
| B-25 | 0.0192 | 0.422 | 22 | Uniform structure | 0.0192 | 0.384 | 20 | Uniform structure | 0.0192 | 0.211 | 11 | Uniform structure |
| B-26 | 0.0192 | 0.403 | 21 | " | 0.0192 | 0.384 | 20 | " | 0.0192 | 0.230 | 12 | " |
| B-27 | 0.032 | 0.480 | 15 | " | 0.032 | 0.416 | 13 | " | 0.032 | 0.224 | 7 | " |
| B-28 | 0.040 | 0.640 | 16 | Nonuniform structure | 0.040 | 0.480 | 12 | " | 0.040 | 0.320 | 8 | " |
| B-29 | 0.040 | 0.640 | 16 | " | 0.040 | 0.480 | 12 | " | 0.040 | 0.280 | 7 | " |

What is claimed is:

1. In the manufacture of steel plate of at least 15mm thickness comprising the steps of casting a molten steel, rolling the obtained ingot or slab into a steel plate and cooling the as-rolled steel plate at such a rate that the center portion of the steel plate is cooled at a rate lower than 6°C/sec, a method for judging, whether or not, the chemical composition of the molten steel is suitable for a particular casting practice, said method comprising the steps of:

measuring the manganese and phosphorous concentrations of the molten steel to be cast;

calculating the product of the manganese and phosphorous concentrations;

comparing said product to be the value of $0.60/f$, wherein $f$ is a segregation factor inherent to said particular casting practice and has been previously determined; and, if said product is larger than $0.60/f$, deciding not to conduct said particular casting practice, and if said product is less than $0.60/f$, deciding to conduct the same, thereby preventing the segregated portion of the rolled steel plate from being transformed into bainite and/or martensite in the course of said cooling step of the plate.

* * * * *